(12) United States Patent  (10) Patent No.: US 7,081,111 B2
Svaasand et al.  (45) Date of Patent: Jul. 25, 2006

(54) CRYOSURGICAL APPARATUS AND METHODS

(75) Inventors: Lars Othar Svaasand, Trondheim (NO); Reinold Ellingsen, Heimdal (NO); Hans Christian Boldstad, Trondheim (NO); Dag Roar Hjelme, Trondheim (NO)

(73) Assignee: OptoMed. AS, Trondheim (NO)

( * ) Notice: Subject to any disclaimer, the term of this patent is extended or adjusted under 35 U.S.C. 154(b) by 300 days.

(21) Appl. No.: 10/146,755

(22) Filed: May 16, 2002

(65) Prior Publication Data

US 2003/0083574 A1  May 1, 2003

(30) Foreign Application Priority Data

May 16, 2001 (GB) .................. 0111986.6

(51) Int. Cl.
A61B 18/02 (2006.01)
(52) U.S. Cl. .......................... 606/21; 606/24
(58) Field of Classification Search .......... 607/96–102; 606/41–50, 1–2, 13–16, 20–26
See application file for complete search history.

(56) References Cited

U.S. PATENT DOCUMENTS

| | | | | |
|---|---|---|---|---|
| 4,397,314 A | * | 8/1983 | Vaguine ....................... | 607/104 |
| 4,967,765 A | * | 11/1990 | Turner et al. ................ | 607/154 |
| 4,988,163 A | * | 1/1991 | Cohen et al. ................. | 385/31 |
| 5,269,777 A | | 12/1993 | Doiron et al. ................. | 606/7 |
| 5,344,435 A | | 9/1994 | Turner et al. ................ | 607/101 |
| 5,437,673 A | | 8/1995 | Baust et al. .................. | 606/23 |
| 5,454,794 A | * | 10/1995 | Narciso et al. ............... | 607/88 |
| 5,509,929 A | | 4/1996 | Hascoet et al. .............. | 607/101 |
| 5,620,480 A | * | 4/1997 | Rudie .......................... | 607/101 |
| 5,647,868 A | * | 7/1997 | Chinn .......................... | 606/21 |
| 5,662,643 A | * | 9/1997 | Kung et al. .................... | 606/3 |
| 5,895,356 A | * | 4/1999 | Andrus et al. .............. | 600/439 |
| 5,899,897 A | * | 5/1999 | Rabin et al. .................. | 606/21 |
| 5,906,612 A | | 5/1999 | Chinn .......................... | 606/20 |
| 5,957,917 A | | 9/1999 | Doiron et al. ................. | 606/7 |
| 6,004,269 A | * | 12/1999 | Crowley et al. ............. | 600/439 |
| 6,017,361 A | | 1/2000 | Mikus et al. ................ | 607/105 |
| 6,056,744 A | * | 5/2000 | Edwards ....................... | 606/41 |
| 6,083,166 A | * | 7/2000 | Holdaway et al. .......... | 600/439 |
| 6,139,544 A | * | 10/2000 | Mikus et al. .................. | 606/21 |
| 6,142,991 A | | 11/2000 | Schatzberger ................ | 606/21 |
| 6,146,378 A | * | 11/2000 | Mikus et al. .................. | 606/21 |
| 6,190,378 B1 | * | 2/2001 | Jarvinen ....................... | 606/21 |
| 6,283,959 B1 | * | 9/2001 | Lalonde et al. ............... | 606/21 |
| 6,379,348 B1 | * | 4/2002 | Onik ............................ | 606/21 |
| 6,562,030 B1 | * | 5/2003 | Abboud et al. .............. | 606/21 |
| 6,690,976 B1 | * | 2/2004 | Fenn et al. .................. | 607/101 |

FOREIGN PATENT DOCUMENTS

| | | |
|---|---|---|
| EP | 0 395 307 | 4/1990 |
| EP | 0 761 257 | 8/1996 |
| EP | 0 792 663 | 9/1997 |

(Continued)

*Primary Examiner*—Roy D. Gibson
(74) *Attorney, Agent, or Firm*—McCormick, Paulding & Huber LLP

(57) ABSTRACT

An apparatus for controlling the temperature of a part of a human or animal body 2 during a cryosurgical procedure is disclosed. The apparatus comprises a radiative energy transmitter 26 for radiating energy to a zone of the body 2 to be protected from excessive cooling. There is also provided a means 12 for controlling the energy radiated by said radiative energy transmitter 26. Preferably the radiative energy transmitter comprises an infra-red laser diode coupled to a diffuser 34 by an optical fibre 40.

29 Claims, 4 Drawing Sheets

FOREIGN PATENT DOCUMENTS

| | | |
|---|---|---|
| JP | 2000296181 | 10/2000 |
| RU | 2153866 | 10/2000 |
| WO | WO 99/15092 | 4/1999 |
| WO | WO 00/72773 | 12/2000 |
| WO | WO 01/10364 | 2/2001 |
| WO | WO 01/18513 | 3/2001 |

* cited by examiner

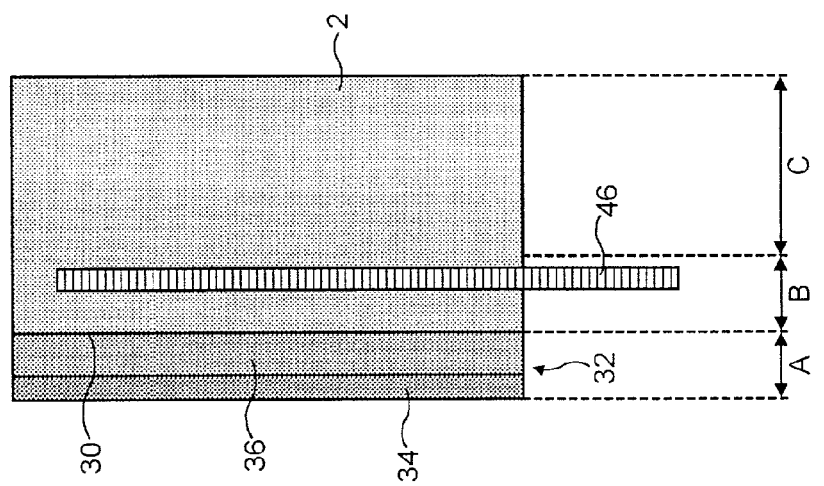
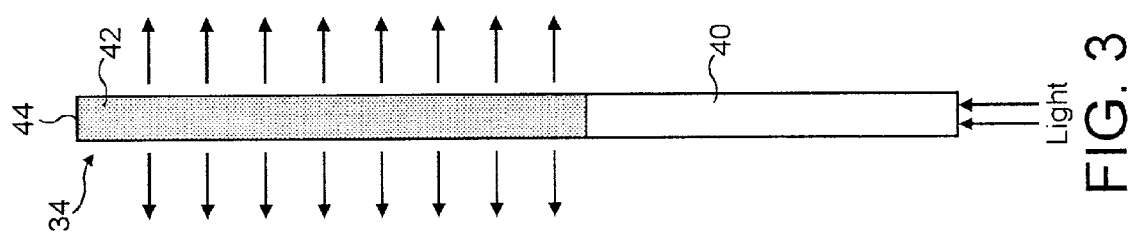

CRYOSURGICAL APPARATUS AND METHODS

This application is entitled to the benefit of and incorporates by reference essential subject matter disclosed in UK Patent Application No. 0111986.6 filed on May 16, 2001.

BACKGROUND

This application relates to apparatus for and methods of performing cryosurgery and in particular to the prevention of damage to tissue surrounding that which is being treated.

Cryosurgery is a modality utilising freezing for ablation of unwanted tissue—e.g. that of a tumour. Clinical experience indicates that for the best results and to ensure proper ablation of the necessary tissue, the tissue should be cooled below about −40° C. The effectiveness may be further enhanced by thereafter allowing the tissue to thaw and repeating the freezing process.

Cryosurgery has great potential for effective treatment of a number of diseases, but does presently face some problems which limit the degree to which it is currently utilised. The major problem facing those who wish to use cryosurgery is effective control of the freezing zone. Clearly, it is important that the surgeon ensures that the whole of the affected tissue is cooled by a sufficient amount whilst avoiding, as far as possible, damage to adjoining tissue through inadvertent freezing.

The most common way for inducing the requisite cooling is to insert a plurality of metal cryoprobes into the vicinity of the tissue to be frozen. These are then cooled down to typically −200° C. using liquid nitrogen or adiabatic expansion of a highly pressurised gas such as argon. The tissue is cooled by thermal conduction from each of the cryoprobes and thus, in practice, an ice ball forms at the tips of the probes and grows in size to encompass the tissue to be frozen. The exact shape of the ice ball will clearly depend partly upon the distribution of the cryoprobes. Its shape will also depend on other factors such as the thermal conductivity of the tissue, the thermal diffusivity of the tissue and blood perfusion and the extent to which these parameters are anisotropic.

One way to control the growth of the ice ball is to generate an ultrasonic image of the treatment site and to use this to judge when the ice ball has grown to an appropriate size. The progress of the ice ball may be seen as a contrast between the frozen and unfrozen tissue. However, it will be appreciated that this will show only tissue which is at freezing point and therefore gives no information as to the temperature reached by tissue within the ice ball, i.e. whether it is has achieved the required −40° C.

Furthermore, the applicants have appreciated that there is a very high thermal inertia associated with the heat conduction and phase transition processes involved which means that significant skill is required on the part of the surgeon to remove the source of cooling agent sufficiently in advance of the ice ball actually reaching the boundary of healthy tissue to take account of its continued growth after the source of cooling has been removed.

It is possible to model the thermal behaviour of the tissue in order to predict where to place the cryoprobes to try to attain the desired temperature distribution and also to try to predict when to remove the source of cooling. An example of such a method is given in U.S. Pat. No. 5,647,868. Whilst being an apparently promising approach, it is beset with a number of problems and is not sufficiently accurate to be relied upon in real use.

Firstly, the thermal properties of bodily tissue tend to be highly inhomogeneous, thereby making the task of specifying the parameters extremely difficult and the resultant model extremely complicated. Furthermore, the thermal parameters are strongly temperature dependent which means that the model is highly non-linear. To give an example, the applicants have found experimentally that the thermal conductivity of bovine muscle frozen to about −20° C. is approximately three times larger than the corresponding value at 37° C. The thermal diffusivity of such tissue exhibits even larger changes—for example the diffusivity at −20° C. is almost four times larger than that at 37° C. Significant changes continue to occur as the tissue is cooled further down towards −200° C.

It is also found experimentally that there is no precisely defined freezing point in bodily tissue. Tissue starts to form ice crystals at −0.5° C. and the process continues to about −10° C. However, there is always approximately 10% of water within the tissue which never forms ice crystals. There is, therefore, no well-defined phase transition temperature as in the case of pure water.

In spite of these difficulties, the Applicants have developed a model in order to demonstrate some of the problems inherent in current cryosurgical techniques. In planar geometry, the propagation of the freezing zone may be modelled as follows. The tissue is assumed to be semi-infinite and homogenous. It is also assumed that the tissue is at a constant initial temperature. The distance, X, of the frozen front from the applicator at time t is given by the following expression:

$$X = 2\lambda \sqrt{\chi_1 t} \qquad (\text{Eq 1})$$

where $\chi_1$ is the thermal diffusivity of the frozen tissue (assumed to be temperature independent). The parameter $\lambda$ characterises the properties of the freezing front—i.e. the interface between frozen and unfrozen tissue—and is therefore dependent on the thermal properties of the frozen and unfrozen tissue, the freezing point and latent heat of freezing (L) of the tissue and on the temperatures of the applicator and tissue respectively.

Table 1 gives some values for the parameter $\lambda$ for various values of the applicator temperature. $\lambda$ is calculated using realistic values for the various parameters, the values being given below Table 1. The symbols used for these parameters throughout are as follows:

$\chi$ = thermal diffusivity (m²/s)
K = thermal conductivity (W/mK)
L = latent heat (J/kg)
T = temperature The table also gives the time taken in minutes for the planar freezing front to travel a distance of 2.5 mm, 5 mm and 10 mm respectively from the applicator for the various applicator temperatures.

TABLE 1

| Applicator temperature in deg. C. | Parameter $\lambda$ | Distance 2.5 mm, Time in min. | Distance 5 mm, Time in min. | Distance 10 mm, Time in min. |
| --- | --- | --- | --- | --- |
| −200 | 0.730 | 0.11 | 0.44 | 1.7 |
| −150 | 0.652 | 0.14 | 0.55 | 2.2 |
| −100 | 0.548 | 0.19 | 0.77 | 3.1 |
| −50 | 0.394 | 0.37 | 1.5 | 6.0 |
| −40 | 0.351 | 0.47 | 1.9 | 7.5 |
| −30 | 0.301 | 0.64 | 2.6 | 10 |
| −20 | 0.239 | 1.0 | 4.1 | 16 |
| −10 | 0.155 | 2.4 | 9.6 | 39 |

$\chi_{frozen} = 4.5 \cdot 10^{-7}$ m²/s
$\chi_{nonfrozen} = 1.2 \cdot 10^{-7}$ m²/s
$K_{frozen} = 1.5$ W/mK
$K_{nonfrozen} = 0.5$ W/mK
L = $2.5 \cdot 10^5$ J/m³ (80% water)
$T_{freeze} = -0.5°$ C.
$T_{normal} = 37°$ C.

As mentioned previously, the thermal diffusivity ($\chi$) is significantly higher in frozen tissue than in unfrozen tissue. This phenomenon compensates for the tendency for the velocity of the freezing front to be reduced as a result of the required latent heat of freezing.

Substituting a cylindrical applicator which is assumed to be infinitely long, the results in Table 2 are achieved for various values for the power drained out per centimetre along the applicator.

TABLE 2

| Power drained out, in W/cm length | Parameter $\lambda$ | Distance 2.5 mm, Time in min. | Distance 5 mm, Time in min. | Distance 10 mm, Time in min. |
|---|---|---|---|---|
| 10 | 0.515 | 0.2 | 0.9 | 3.5 |
| 8 | 0.464 | 0.3 | 1.1 | 4.3 |
| 6 | 0.402 | 0.4 | 1.4 | 5.7 |
| 4 | 0.319 | 0.6 | 2.3 | 9.1 |
| 2 | 0.198 | 1.5 | 5.9 | 24 |

$\chi_{frozen} = 4.5 \cdot 10^{-7}$ m$^2$/s
$\chi_{nonfrozen} = 1.2 \cdot 10^{-7}$ m$^2$/s
$K_{frozen} = 1.5$ W/mK
$K_{nonfrozen} = 0.5$ W/mK
$L = 2.5 \cdot 10^5$ J/m$^3$ (80% water)
$T_{freeze} = -0.5°$ C.
$T_{normal} = 37°$ C.

When the applicator is removed, the situation may be modelled as a semi-infinite uniformly frozen tissue brought into contact with semi-infinite non-frozen tissue. Again, the distance, R, of the propagating frozen zone can be expressed by:

$$R = 2\lambda\sqrt{\chi_1 t} \qquad \text{(Eq 2)}$$

This time, however, $\lambda$ is as given in Table 3. This also gives the time in minutes for the freezing front to continue to propagate a distance of 2.5 mm, 5 mm and 10 mm respectively.

TABLE 3

| Initial temperature of frozen tissue, in deg. C. | Parameter $\lambda$ | Distance 2.5 mm, Time in min | Distance 5 mm, Time in min | Distance 10 mm, Time in min |
|---|---|---|---|---|
| −200 | 0.448 | 0.3 | 1.1 | 4.6 |
| −150 | 0.364 | 0.4 | 1.7 | 7.0 |
| −100 | 0.255 | 0.9 | 3.6 | (14) |
| −50 | 0.105 | 5.2 | (21) | (84) |
| −40 | 0.067 | (12.9) | (52) | (1608) |
| −30 | 0.024 | (100) | (402) | (6400) |
| −24.2 | 0 | ∞ | ∞ | ∞ |
| >−24.2 | Negative | Thawing | Thawing | Thawing |

$\chi_{frozen} = 4.5 \cdot 10^{-7}$ m$^2$/s
$\chi_{nonfrozen} = 1.2 \cdot 10^{-7}$ m$^2$/s
$K_{frozen} = 1.5$ W/mK
$K_{nonfrozen} = 0.5$ W/mK
$L = 2.5 \cdot 10^5$ J/m$^3$ (80% water)
$T_{freeze} = -0.5°$ C.
$T_{normal} = 37°$ C.

From this it will be seen that there is a value of the initial temperature of the frozen tissue which gives a value for $\lambda$ of 0 thereby representing a critical temperature for the frozen tissue, below which the freezing zone will continue to propagate after the applicator is removed, but above which the freezing zone will not continue to propagate. Of course, it will be appreciated that the critical value in this model is a higher temperature than that which is required to ablate malignant tissue effectively (i.e. approx −40° C.) and thus, conversely, if the present tissue is at a sufficiently low temperature, the freezing zone will continue to propagate.

Eventually the freezing zone will retreat as the tissue thaws again. The retreat of the freezing front will, however, be much slower than its advance. There are several reasons for this. Firstly, the thermal diffusivity in non-frozen tissue is, as mentioned above, significantly lower than in frozen tissue. Secondly, the transfer of latent heat of melting slows the process. Thirdly, the temperature difference between freezing point (e.g. −0.5° C.) and 37° C. is much less than the difference between the freezing point and an applicator at −200° C. In an example of the above, the velocity of propagation of the thawing zone in the case of a 40° C. applicator brought into contact with tissue frozen down to −200° C. would be only 7% of the velocity of the freezing boundary in the opposite direction when a −200° C. applicator is applied.

It should be borne in mind that the above models do not take blood perfusion into account. Blood perfusion also introduces an uncertain factor if included in a thermal model of tissue. During the freezing process, blood vessels are occluded and the blood circulation is shut down. After thawing, an edema develops in the outer margins of the frozen region and blood perfusion does not necessarily return to its original value. The perfusion in such margins can, therefore, be different during successive freezing periods.

Blood perfusion will tend to speed up the thawing process and the effect is likely to dominate at timescales longer than the blood perfusion relaxation time, typical values for which are 5–10 minutes in muscle tissue and 20–30 minutes in poorly perfused adipose tissue. The figures given in brackets in Table 3 are those which may be significantly affected by blood perfusion.

It will be seen from the above that there is a significant problem in the practical application of cryosurgery that thermal perturbations are highly diffused—i.e. smoothed out with time and distance from the source of the perturbation (e.g. the cryoapplicator). The problem can be reduced by minimising the distance between the applicator and the edge of the tissue which is to be frozen, but the extent to which this may be done is limited by the number of applicators required. Typically, the distance between an applicator and the edge of the affected tissue is of the order to 10 mm–15 mm.

It can be established from the crude models set out previously that in practical techniques the propagation of the freezing boundary towards the edge of the desired tissue cannot be stopped instantaneously—e.g. by cutting off the flow of cryogen thereto. There will be a time delay before any change of the applicator condition will have an influence on the edge of the freezing boundary.

It can be shown that in the above models this time delay is proportional to the square of the distance between the boundary and the cryoapplicator and inversely proportional to the thermal diffusivity of the frozen tissue. Thus, for a distance in the range of 10 mm–15 mm, the delay is of the order of 4–8 minutes. The freezing boundary will, of course, propagate several millimetres during this time. It is therefore necessary for the surgeon to judge when to adjust the cooling conditions significantly before the outer limit of the freezing zone is reached.

It is possible to protect some healthy body structures by passing heated water through them in order to prevent freezing thereof. In one particular example, water at approximately 37° C. may be passed through the urethra during cryosurgical ablation of the prostate. This solution is, however, limited by the maximum temperature which can be tolerated by the healthy tissue structure, which is only approximately 45° C. The rate of heat conduction into the tissue is therefore relatively low. Furthermore, the water is soon cooled and thus its temperature can differ significantly along the length of the region it is designed to protect. A discussion of this problem and an attempt at a solution thereof is given in U.S. Pat. No. 6,017,361. There remains, however, the limitation that this approach can only be used to protect structures in the vicinity of regions through which heated water can be passed.

The maximum temperature of such water which may be tolerated in the human body in order to prevent hyperthermia or protein denaturation is approximately 45° C. On the other hand, successful cryotherapy requires temperatures which are no greater than approximately −40° C. to −50° C. Significant amounts of power are required to maintain such a large temperature drop across only approximately 3 mm–5 mm of tissue. Typically, a power density of 1W–2W per square centimetre is required to maintain this thermal gradient. This would require a high flow rate and effective thermal transfer between the water and the tissue to be protected.

Where a critical structure within the body is protected by passing water either at body temperature or a slightly elevated temperature through a suitable tube the separation between the temperature source and the freezing boundary may be significantly smaller than between a cryoapplicator and the freezing zone, e.g. of the order of 3 mm–5 mm, but the time delay in such cases is still significant since the relevant diffusivity is that of non-frozen tissue which, as stated earlier, is significantly lower than that in frozen tissue. Thus, although the distance is reduced by a factor of three as compared to the cryoapplicator time delay, the heating time delay is only reduced by approximately 50% due to this reduced thermal diffusivity and so is of the order of 2–4 minutes.

It is an object of the present invention to provide an improved way of protecting surrounding body tissue during cryosurgery.

SUMMARY OF THE INVENTION

When viewed from a first aspect the present invention provides an apparatus for controlling the temperature of a part of the human or animal body during a cryosurgical procedure comprising a radiative energy transmitter for radiating energy to a zone of the body to be protected from excessive cooling and means for controlling the energy radiated by said emitter.

When viewed from a second aspect, the invention provides a method of controlling the temperature of a part of the human or animal body during a cryosurgical procedure to protect said part from excessive cooling, comprising radiating energy to said part from a radiative energy transmitter and controlling the energy radiated by said emitter to prevent said excessive cooling.

The invention also extends to a method of treatment of the human or animal body comprising freezing a portion of the tissue thereof and radiating energy from a radiative transmitter to another portion of tissue to prevent excessive cooling thereof.

Thus it will be seen by those skilled in the art that in accordance with the present invention, parts of the body which are to be protected from freezing during cryosurgery may be heated radiatively by a suitable radiative energy emitter. The huge advantage that this offers over known arrangements is that the timescales involved in such radiative heating are negligible in comparison to the timescale for thermal influences to be conducted through body tissues. In the example given above there is a time lag of the order of 4 to 8 minutes between removal of the source of cooling agent and contraction of the ice ball which prohibits effective real-time control.

By contrast, in accordance with the present invention, in which energy may be radiated directly to critical structures within the body, the rate of energy transfer to the area in question may be of the order of $10^3$m/S in the case of acoustic energy which would give a time delay under the conditions given above of the order of 10 µs. Alternatively and preferably, electromagnetic radiation is used which will give a negligible time delay since this will propagate at the speed of light. This means that dynamic control of the freezing process may be exercised—e.g. by an operator monitoring progress of the ice ball—so as to prevent damage to critical structures.

It will also be appreciated that with the possibility of accurate dynamic control of the freezing process, a reduced number of cryoapplicators is needed since heating by the radiative energy emission may be used to shape the temperature profile rather than relying predominantly on the cryoapplicators. This is clearly beneficial from a resources point of view, but also increases comfort for the patient.

Similarly, a reduced reliance on producing a precise temperature distribution means that the placement of each cryoapplicator is less critical than in known arrangements. This makes it possible that the applicators may be placed in accordance with a predictive model, albeit relatively inaccurately.

In the case of electromagnetic radiation, the energy will be absorbed as it propagates and will therefore decay exponentially. The penetration depth is defined as the depth into the tissue at which the amplitude of the radiation is reduced to 1/e of its original value—i.e. 37%. Typically the penetration depth is 10 mm–30 mm for microwave radiation, about 3 mm–5 mm for near infrared radiation and about 0.5 mm–1 mm for visible light (yellow/green/blue). Thus, the frequency of the radiation may be tailored to give the desired penetration depth depending upon the critical structure which is being protected and its thickness.

By accurate control of the amplitude and frequency of the radiation, the rate of heating and the penetration depth respectively may similarly be accurately controlled.

Preferably infrared, most preferably near infrared, radiation is employed since this gives a penetration depth of the order of the thickness of the typical boundary layer to be protected. Furthermore, equipment for generating and guiding such radiation is easily available, highly reliable and comparatively inexpensive.

Preferably, a laser diode is used to generate the radiation. It is also preferred to employ an optical fibre to guide the radiation to the required point of delivery. Thus the radiative emitter preferably comprises an emission portion and an optical fibre coupling said emission portion to a remote radiation source, preferably a laser diode. Alternatively the optical fibre could itself comprise a fibre laser.

The radiative emitter is preferably arranged to emit radiation substantially normally from an elongate emission portion. The emission portion is cylindrical in the preferred embodiment and in that case therefore such emission would be substantially radial. Most preferably the emitter comprises a cylindrical diffuser for converting light introduced longitudinally at an end thereof into radially emitted light. It will be appreciated that a series of such emitters may be provided side-by-side in order to give an essentially planar emitting slab. Such slab could be arranged to emit radiation in one direction only—e.g. with a suitably reflective coating on one side.

In a preferred application of the invention, cryoablation of a prostate tumour is contemplated and a suitable transmitter is inserted into the urethra to protect it against freezing. Preferably therefore the radiative emitter is suitable for in-vivo use i.e. by being sterile.

Although the radiated energy may be used on its own to provide thermal protection, preferably a heated liquid, e.g. water, is also used. In preferred embodiments the radiative emitter comprises a preferably integral conduit for passing a heated liquid into a body into which the emitter is inserted.

The radiative emitter may be used to heat tissue which is to be protected in accordance with a predetermined heating profile—e.g. as calculated from a mathematical model. Preferably however, at least one temperature sensing means is provided in order to provide feedback on the temperature at a given point—e.g. a critical structure within the body. Such feedback may be manual in the sense that the information is presented to an operator who uses this to control the supply of energy to the energy emitter.

Alternatively, an algorithm may be defined for adjusting the supply of energy at least partially automatically on the basis of the feedback. The significant advantage of this arrangement is that much less reliance on mathematical modelling is required in order to provide adequate thermal protection of critical tissue surrounding the freezing site. It will be appreciated from a consideration of the many factors mentioned earlier which make accurate modelling so difficult, that being able to reduce the reliance on such models is a substantial benefit. It should be appreciated that such real-time feedback is enabled by the rapid energy propagation associated with the present invention.

The applicants have further appreciated that whereas previously temperature monitoring of as much of the tissue as possible was necessary in order to provide comprehensive data to the model to increase its accuracy, in accordance with the preferred embodiments of the present invention, only those structures surrounding the proposed freezing zone which it is critical to protect, need be monitored.

In preferred embodiments, means are provided for suggesting locations for placement of one or more cryoapplicators. Preferably, such means comprises a predictive model which may be fed with information such as the size of the zone (e.g. tumour) to be frozen, the body temperature and the like. It will be appreciated that this still requires the use of a mathematical model, but nonetheless the arrangement is beneficial over known ones since the initial prediction may be relatively less accurate given that dynamic control of the heating/cooling process is possible in accordance with the invention.

In accordance with the preferred method, the radiative emitter is preferably inserted into the urethra in order to provide thermal protection thereof during cryoablation of the prostate gland. Additionally or alternatively, a or the radiative emitter is inserted into the patient's rectum in order to give thermal protection to the rectal wall.

In addition to temperature sensing means, means for imaging the tissue to be treated and the surrounding tissue is preferably provided. Preferably such means comprises an ultrasonic transmitter and receiver which are used to generate an ultrasound image as is well known in the art.

BRIEF DESCRIPTION OF THE DRAWINGS

Certain preferred embodiments of the present invention will now be described, by way of example only, with reference to the accompanying drawings in which:

FIG. 3 is a view similar to FIG. 2 but including a temperature probe;

FIG. 4 is an enlarged view of an optical radiative emitter in accordance with the invention.

DESCRIPTION OF THE PREFERRED EMBODIMENTS

Figure 1:
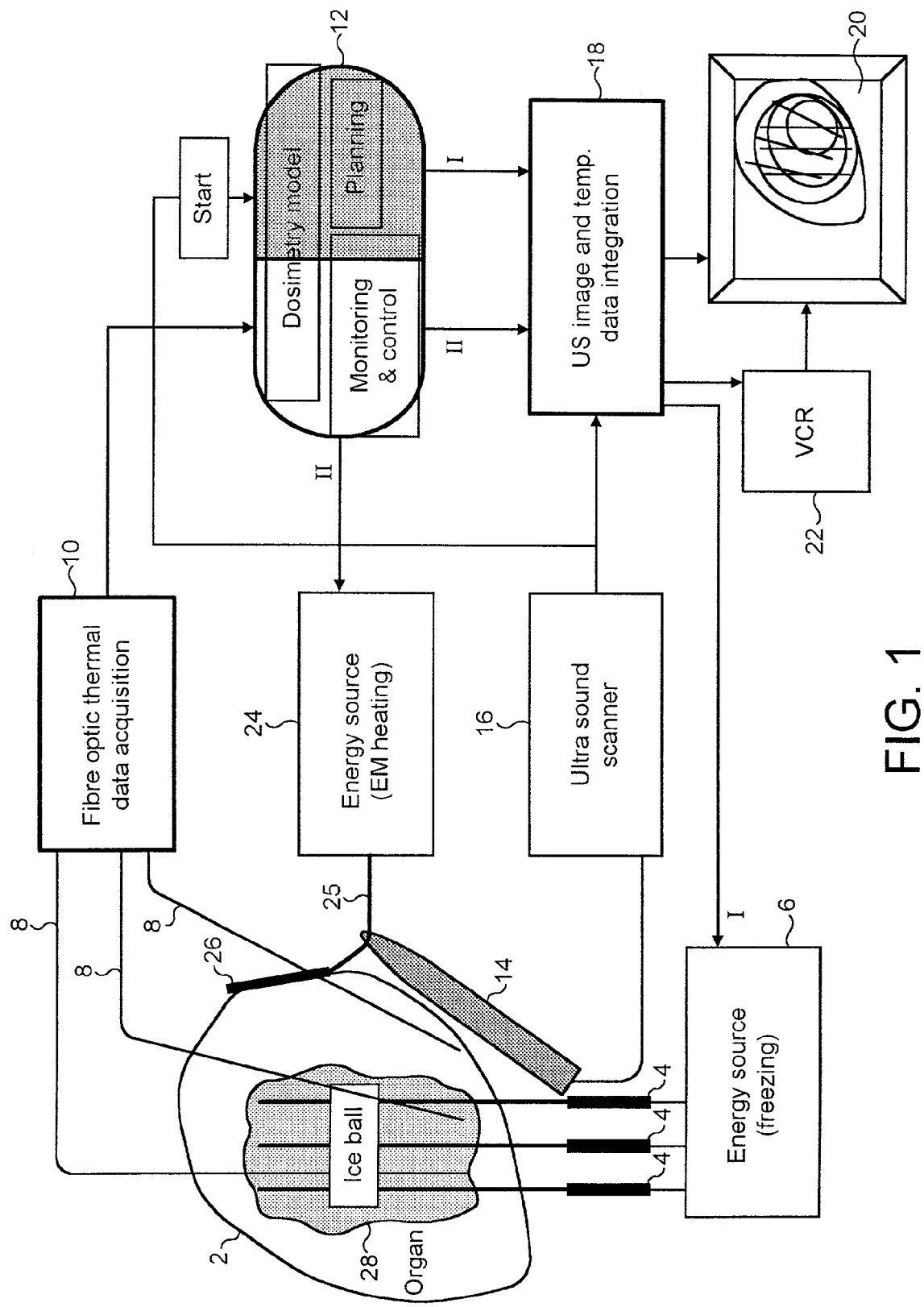
FIG. 1 is a schematic block diagram of a thermal dosimetry system in accordance with the invention.

Turning to FIG. 1 there may be seen a schematic block diagram of a thermal dosimetry system in accordance with the invention. A schematic representation of a patient's prostate gland is indicated by the reference numeral 2. A series of cryoapplicators 4 are inserted into the organ 2. These may be any commercially available applicators of the sort well known in the art. These function by allowing the expansion of highly pressurised argon gas from a gas source 6. Also inserted into the organ 2 are a series of fibre optic temperature probes 8 for monitoring temperature within the organ 2. These probes are described in greater detail in WO 01/18513 to which reference should be made for further information.

The fibre optic thermal probes 8 are interrogated by a thermal data acquisition unit 10 the output of which is fed into a computer 12 on which the thermal properties of the organ 2 are modelled mathematically.

Also provided in the proximity of the organ 2 is an ultrasound probe 14 of known type which is driven by a scanning unit 16 which feeds the resulting image data both to the thermal model 12 and an integration unit 18. The integration unit 18 integrates the thermal information received from the dosimetry model 12 and the ultrasound image information from the ultrasound scanner 16 and uses these to produce a visible image on a screen 20 showing the pattern of isotherms overlaid on the actual image of the organ 2. This image may be recorded on a video cassette recorder 22. The integration unit 18 is also connected to the cryoapplicator driving unit 6 which makes it possible for the integration unit 18 to control the cryoapplicators 4.

As well as providing thermal information for integration with the visible image by the integration unit 18, the computer model 12 monitors the temperature of critical structures within the organ 2 in the proximity of the desired freezing zone which must be protected from freezing. This temperature information is used by a predefined algorithm to control an energy source 24 which contains a laser diode. This is optically coupled, by means of an optical fibre 25, to a radiative emitter 26 comprising a cylindrical diffuser and inserted into the patient's urethra. A suitable diffuser is available from Medlight SA of Ecublens of Switzerland under the product name 'Radial Light Distributor'.

In operation, the temperature probes 8 and ultrasound probe 14 are inserted into the patient and used to provide data to the computer model 12 as to the size and temperature profile of the organ 2. This is then used by the computer model 12 to predict optimum positions for the cryoapplicators 4. These predicted positions are overlaid onto the ultrasound image 20 to facilitate correct placement of the cryoapplicators 4 by the surgeon.

Once the cryoapplicators 4 have been inserted, the driving unit 6 supplies highly pressurised argon gas to the cryoapplicators 4. The gas undergoes rapid adiabatic expansion at the ends of the cryoapplicators, reducing the temperature thereof to −200° C. This causes an ice ball 28 to begin to form in the tissue of the organ 2 around the tips of the cryoapplicators 4.

As the ice ball 28 grows, the temperature of critical structures within the organ 2 is monitored by means of the temperature probes 8. Should the temperature of any of the structures become too low, e.g. to put them in danger of freezing, this fact is recognised by the computer model 12 which issues an appropriate instruction to the energy source 24 driving the emitter probe 26 to cause the power level thereof to be increased in order to further heat the critical structure to reduce the danger of it freezing. Since the required energy is radiated to the tissue of the critical structure from the emitter 26 effectively instantaneously, the appropriate remedial heating is effected straight-away before the temperature of the critical structure drops any further. Thus, rapid dynamic control of the temperature of the critical structures is achieved.

Progress of the ice ball may be monitored visually as a contrast between the frozen and unfrozen tissue which shows up on the ultrasound image 20. This allows the surgeon to determine when the ice ball has grown to a sufficient size to ensure effective ablation of the required tissue. The supply of cooling agent by the driving unit 6 should be stopped some time before the desired size of ice ball 28 is reached since the perimeter of the ice ball will continue to expand even after the cooling agent supply is stopped. However, it is not critical that the cooling agent is stopped at precisely the right time since subsequent expansion of the ice ball 28 may be controlled by the emitter probe 8.

Figure 2:
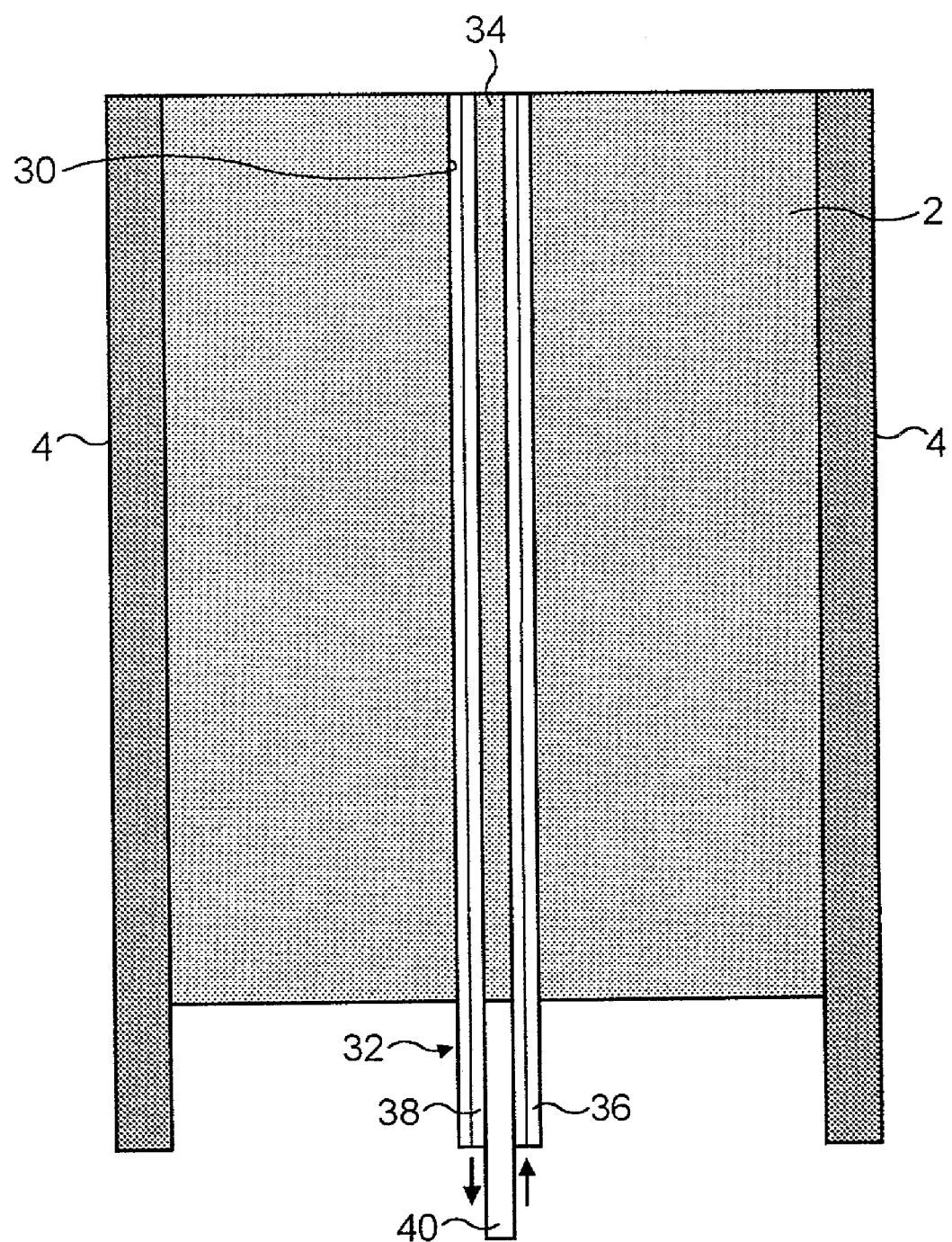
FIG. 2 is an enlarged, schematic cross-sectional view of an embodiment of the invention being used in the cryotreatment of a prostate.

Turning to FIG. 2, there may be seen an enlarged, schematic cross-sectional view of the use of apparatus in accordance with the invention to perform cryotherapy on a diseased prostate gland 2. From the diagram, there may be seen a pair of cryoapplicators 4 which are inserted into the prostate gland 2 of a patient. The urethra 30 may be seen running through the centre of the section of the prostate gland 2 shown in the diagram. An optically transparent tube 32 is inserted into the urethra 30. A cylindrical light diffuser 34 (shown in greater detail in FIG. 3) is mounted within the tube. Two annular spaces 36, 38 outwardly of the diffuser 34 are provided to allow water to circulate within the tube 32. Water at 37° C. enters the outermost annular space 36 and flows up it thereby helping to maintain the temperature of the wall of the urethra. At the distal end of the tube 32 (not shown) the water is transferred to the inner annular space 38 for its return to the proximal end of the tube 32 where it exits.

An optical fibre 40 is coupled to the proximal end of the diffuser 34 in order to transfer light into it. In use, near infrared light is generated in an energy source 24 (see FIG. 1) and the light is then passed along the optical fibre 40 and into the cylindrical diffuser 34. As may be seen in FIG. 3, the cylindrical diffuser 34 comprises a transparent flexible polymer in which is embedded an array of scattering particles—e.g. sapphire granules 42. A suitable such cylindrical diffuser is available from Medlight SA of Ecublens of Switzerland under the name 'Radial Light Distributor'. As light entering the diffuser 34 from the optical fibre 40 comes into contact with the scattering particles 42, it is scattered in random directions which will cause a net radial outflux of light. The distal end 44 of the diffuser is provided with a reflective coating in order to reflect any light which would otherwise exit at that point back into the diffuser 34 to be scattered radially outwardly.

FIG. 4 shows one half of a diagram similar to that shown in FIG. 2 in which the urethra is thermally protected during cryosurgery performed on prostate tissue 2. This diagram highlights the differing thermal regimes within the tissue. Thus, it may be seen that the temperature within the tube 32 up to the urethra wall 30 (zone A) is dominated by water flow in the annular space 36 outwardly of the cylindrical diffuser 34.

Moving leftwards from the urethra wall 30, the temperature of the prostate tissue 2 is initially dominated by the effect of heating of the tissue by the near infra-red radiation emitted from the cylindrical diffusers 34 penetrating the prostate tissue 2 (zone B). Since the prostate tissue 2 absorbs the infra-red radiation, the amplitude thereof will decay exponentially the characteristic penetration depth of the radiation is defined as the distance required for the amplitude to fall to 1/e of its initial value. For radiation in the near infra-red band, the penetration depth in prostate tissue is approximately 3 mm–5 mm.

Beyond this (zone C), the heat drained by the cryoapplicator (not shown) begins to dominate the temperature of the tissue.

FIG. 4 additionally shows a temperature sensing probe 46 inserted into the prostate 2. This is a fibre optic temperature sensor such as that disclosed in WO 01/18513. This is placed in close proximity to the urethra 30 in order that its temperature can be monitored and the emission of the radiative emitter 34 can be adjusted accordingly.

Figure 5:
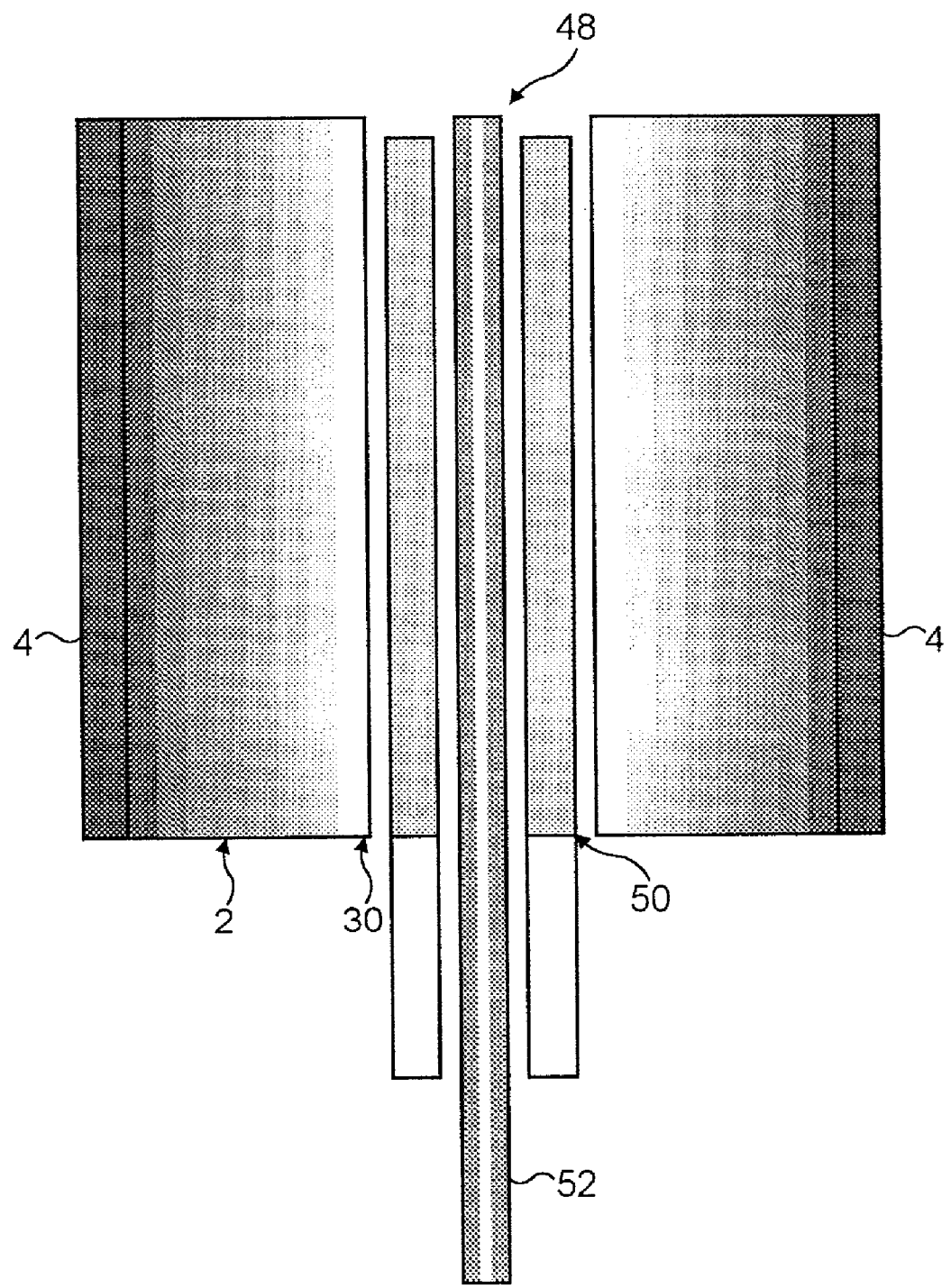
FIG. 5 is a schematic, enlarged cross-sectional view of a further embodiment of the invention employing ultrasonic imaging.

FIG. 5 shows a schematic, enlarged cross-sectional view of a prostate gland 2 undergoing cryosurgery in which a radiative emitter in accordance with another embodiment of the invention is employed. In common with the earlier embodiments, cryoapplicators 4 at approximately −200° C. are used to freeze prostate tissue 2. In this embodiment, a different form of radiative emitter 48 is used. In contrast with the previous embodiments, there is no separate outer tube, but rather the hollow cylindrical diffuser 50 is inserted directly into the urethra 30. As well as the optical emitter 50, an ultrasonic emitter 52 is mounted within the hollow cylindrical diffuser 50. The ultrasonic emitter 52 allows a visual monitoring of the propagation of the freezing front of the ice ball towards the urethra 30 using suitable ultrasonic receivers and imaging system of the sort well known in the art. Furthermore, it will be seen that in this embodiment, no forced water flow is used, radiation from the cylindrical diffuser 50 is relied upon to provide thermal protection to the urethra and surrounding critical structures.

It will be appreciated by those skilled in the art that there are many possible variations and modifications to the embodiment described above within the scope of the present invention. For example, rather than infra-red light, other wavelengths of electro-magnetic radiation may be used such as microwaves or visible light, with correspondingly different characteristic penetration depths. Moreover, it is not even necessary to use electromagnetic radiation, acoustic radiation could, instead, be used.

It is, moreover, not essential to use the apparatus of the invention to protect the urethra. Additionally or alternatively, a similar device may be used to protect—e.g. the rectal wall. In this case, a series of optical diffusers may be mounted together to form a slab in order to emit essentially planar radiation.

The invention claimed is:

1. A method of controlling the temperature of part of the human or animal body during a cxyosurgical procedure to protect a zone of said body from excessive cooling by radiating energy to said zone from a radiative energy transmitter and controlling said energy radiated to prevent said excessive cooling.

2. A method according to claim 1, wherein said energy is radiated to said zone in the form of electromagnetic radiation.

3. A method according to claim 2, wherein said energy is radiated to said zone in the form of infra-red radiation.

4. A method according to claim 2, wherein said energy is radiated to said zone in the form of near infra-red radiation.

5. A method according to claim 2, comprising using a laser diode to generate said energy.

6. A method according to claim 2, wherein said radiative energy transmitter comprises an emission portion coupled to a remote radiation source by an optical fiber.

7. A method according to claim 2, wherein said radiative energy transmitter comprises a diffuser converting light introduced longitudinally at an end thereof into light emitted in a direction substantially normal to the face of said diffuser.

8. A method according to claim 2, wherein said energy is radiated to said zone in the form of microwave radiation.

9. A method according to claim 2, wherein said energy is radiated to said zone in the form of radio frequency radiation.

10. A method according to claim 1, wherein said energy is radiated to said zone in the form of acoustic waves.

11. A method according to claim 1, comprising radiating said energy substantially normally from an elongate emission portion.

12. A method according to claim 11, wherein said elongate emission portion is cylindrical and said energy is radiated in a substantially radial direction.

13. A method according to claim 1, comprising using at least one temperature sensor to provide feedback on the temporal and spatial temperature distribution in said zone.

14. A method according to claim 13, comprising sensing said temperature distribution with a fibre optic temperature probe.

15. A method according to claim 13, comprising adjusting the supply of said energy at least partially automatically on the basis of said feedback.

16. A method according claim 13, comprising presenting said feedback to an operator to allow the operator to control the supply of energy to said radiative energy transmitter.

17. A method according to claim 1, comprising passing a heated liquid into said body.

18. A method according to claim 1, comprising inserting said radiative energy transmitter into said body and passing a heated liquid into said body through an integrated conduit.

19. A method according to claim 1, comprising using a predictive model to suggest locations for placement of at least one cryoapplicator.

20. A method according to claim 19, comprising feeding said model with information on the properties of said region to be cooled.

21. A method according to claim 1, comprising using at least one said radiative energy transmitter to shape the temperature profile around at least one cryoapplicator.

22. A method according to claim 1, comprising using a plurality of said energy transmitters aligned side by side in order to give an essentially planar emitting slab.

23. A method according to claim 22, comprising emitting energy from said slab substantially in one direction only.

24. A method according to claim 1, comprising creating an image of said zone.

25. A method according to claim 24, comprising imaging said zone by using an ultrasonic transmitter and receiver.

26. The method according to claim 25, wherein said ultrasonic transmitter is integrated within said radiative energy transmitter.

27. A method of treatment of a human or animal body comprising freezing a portion of tissue thereof and preventing excessive cooling of a zone of tissue by radiating energy from a radiative energy transmitter to said zone of tissue to prevent excessive cooling thereof.

28. A method according to claim 27, comprising inserting said radiative energy transmitter into at a patient's urethra or rectum during cryoablation of a patient's prostate gland to protect the surrounding zones against excessive cooling.

29. A method according to claim 2 wherein said energy is radiated to said zone in the form of visible radiation.

* * * * *

UNITED STATES PATENT AND TRADEMARK OFFICE
CERTIFICATE OF CORRECTION

| | | |
|---|---|---|
| PATENT NO. | : 7,081,111 B2 | Page 1 of 1 |
| APPLICATION NO. | : 10/146755 | |
| DATED | : June 25, 2006 | |
| INVENTOR(S) | : Svaasand et al. | |

It is certified that error appears in the above-identified patent and that said Letters Patent is hereby corrected as shown below:

Column 11, Claim 1, line 6, please delete the word "cxyosurgical" and replace with --cryosurgical--.

Signed and Sealed this

Seventh Day of November, 2006

JON W. DUDAS
*Director of the United States Patent and Trademark Office*